(12) United States Patent
Nishida et al.

(10) Patent No.: US 8,029,690 B2
(45) Date of Patent: Oct. 4, 2011

(54) PROCESS FOR PRODUCTION OF HIGHLY PURE QUATERNARY AMMONIUM SALT

(75) Inventors: Tetsuo Nishida, Izumiotsu (JP);
Kazutaka Hirano, Izumiotsu (JP);
Akinori Oka, Tokushima (JP);
Yoshinobu Abe, Tokushima (JP);
Akihiro Nabeshima, Tokushima (JP)

(73) Assignees: Otsuka Chemical Co., Ltd., Osaka (JP);
Stella Chemifa Corporation, Osaka (JP)

( * ) Notice: Subject to any disclaimer, the term of this patent is extended or adjusted under 35 U.S.C. 154(b) by 310 days.

(21) Appl. No.: 12/311,071

(22) PCT Filed: Sep. 19, 2007

(86) PCT No.: PCT/JP2007/068741
§ 371 (c)(1),
(2), (4) Date: Mar. 18, 2009

(87) PCT Pub. No.: WO2008/035808
PCT Pub. Date: Mar. 27, 2008

(65) Prior Publication Data
US 2009/0272933 A1    Nov. 5, 2009

(30) Foreign Application Priority Data
Sep. 19, 2006   (JP) ................... 2006-252230

(51) Int. Cl.
*H01G 9/02*    (2006.01)
*C07C 209/00*    (2006.01)

(52) U.S. Cl. ...................... 252/62.2; 564/296

(58) Field of Classification Search .............. 252/62.2; 564/296
See application file for complete search history.

(56) References Cited

U.S. PATENT DOCUMENTS
2004/0130852 A1    7/2004   Matsumoto et al.

FOREIGN PATENT DOCUMENTS

| JP | 63-233956   | 9/1988  |
| JP | 2000-26473  | 1/2000  |
| JP | 2000-311839 | 11/2000 |
| JP | 2004-186246 | 7/2004  |
| JP | 2006-143648 | 6/2006  |

OTHER PUBLICATIONS

International Search Report issued Dec. 4, 2007 in the International (PCT) Application of which the present application is the U.S. National Stage.

*Primary Examiner* — Porfirio Nazario Gonzalez
(74) *Attorney, Agent, or Firm* — Wenderoth, Lind & Ponack, L.L.P.

(57) ABSTRACT

A process for preparing a highly pure quaternary ammonium salt comprising:
(1) adding a quaternary ammonium hydroxide salt or quaternary ammonium carbonate to a quaternary ammonium salt containing a protonic acid salt of a tertiary amine as an impurity and thereby neutralizing the tertiary amine protonic acid salt with the quaternary ammonium hydroxide salt or carbonate to convert the acid salt to a tertiary amine and water and to convert the quaternary ammonium hydroxide salt or carbonate to a quaternary ammonium salt at the same time, and
(2) removing the tertiary amine and water produced from the system.

3 Claims, No Drawings

US 8,029,690 B2

PROCESS FOR PRODUCTION OF HIGHLY PURE QUATERNARY AMMONIUM SALT

This application is a U.S. national stage of International Application No. PCT/JP2007/068741 filed Sep. 19, 2007.

TECHNICAL FIELD

The present invention relates to a process for preparing quaternary ammonium salts for use as electrolytes in electric double layer capacitors, electrolytic capacitors and like capacitor elements by reducing the amounts of a tertiary amine and a tertiary amine protonic acid salt contained as impurities in quaternary ammonium salts.

BACKGROUND ART

For preparing quaternary ammonium salts, already known are a process comprising reacting an alkyl halide with a tertiary amine to obtain a quaternary ammonium halide and reacting an acid with the halide, and a process comprising reacting a carbonic acid diester with a tertiary amine to produce a quaternary ammonium salt and subsequently reacting an acid with the salt for decarbonation.

In the case where the tertiary amine is not completely converted to a quaternary compound in either of these processes, the tertiary amine left unreacted will react with the acid in the next step to produce a protonic acid salt of the tertiary amine, permitting the acid salt to remain in the main product of quaternary ammonium salt.

The quaternary ammonium halide or quaternary ammonium salt is likely to produce a tertiary amine when thermally decomposed. The tertiary amine produced provides a tertiary amine protonic acid salt in the process for preparing the quaternary ammonium salt. Since the hydrogen atom of the cation of the tertiary amine protonic acid salt is liable to become released as a proton, the acid salt is unstable to a reducing reaction, so that the acid salt is known to be responsible for the diminution of the voltage resistance and long-term reliability of electric double layer capacitors and electrolytic capacitors (for example, Patent Literature 1).

Accordingly, it is required to reduce the amounts of the tertiary amine and tertiary amine protonic acid salt which are present in quaternary ammonium salts for use as electrolytes in order to obtain highly reliable electric double layer capacitors and electrolytic capacitors.

In reducing the amounts of the tertiary amine and tertiary amine protonic acid salt in quaternary ammonium salts, it is known to recrystallize the salt in an organic solvent (Patent Literature 1, 2).

However, this method is not suitable to practice industrially, for example, because the crystallization leads to a lower yield. Furthermore, it is difficult to effect the recrystallization if the quaternary ammonium salt is a liquid substance at room temperature.

An object of the present invention is to provide a process for preparing quaternary ammonium salts by reducing the amounts of a tertiary amine and a tertiary amine protonic acid salt contained as impurities in quaternary ammonium salts.

[Patent Literature 1] JP2000-311839A

[Patent Literature 2] JP2004-186246A

DISCLOSURE OF THE INVENTION

The present invention provides the following.

1. A process for preparing a highly pure quaternary ammonium salt comprising:

(1) adding a quaternary ammonium hydroxide salt or quaternary ammonium carbonate to a quaternary ammonium salt containing a protonic acid salt of a tertiary amine as an impurity and thereby neutralizing the tertiary amine protonic acid salt with the quaternary ammonium hydroxide salt or carbonate to convert the acid salt to a tertiary amine and water and to convert the quaternary ammonium hydroxide salt or carbonate to a quaternary ammonium salt at the same time, and (2) removing the tertiary amine and water produced from the system.

2. A process for preparing a highly pure quaternary ammonium salt comprising:

(1) reacting a tertiary amine with an alkyl halide having or not having a substituent to obtain a quaternary ammonium halide salt, (2) reacting an acid compound with the halide salt to obtain a quaternary ammonium salt containing a tertiary amine protonic acid salt as an impurity, (3) adding a quaternary ammonium hydroxide salt or quaternary ammonium carbonate to the quaternary ammonium salt and thereby neutralizing the tertiary amine protonic acid salt with the quaternary ammonium hydroxide salt or carbonate to convert the acid salt to a tertiary amine and water and to convert the quaternary ammonium hydroxide salt or carbonate to a quaternary ammonium salt at the same time, and (4) removing the tertiary amine and water produced from the system.

According to the invention, the term a protonic acid salt of a tertiary amine refers to a tertiary amine salt having releasable $H^+$ in the molecule.

The present invention provides a process for preparing a high-purity quaternary ammonium salt which process comprises: (1) adding a quaternary ammonium hydroxide salt or quaternary ammonium carbonate to the quaternary ammonium salt and thereby neutralizing the tertiary amine protonic acid salt with the quaternary ammonium hydroxide salt or carbonate to convert the acid salt to a tertiary amine and water and to convert the quaternary ammonium hydroxide salt or carbonate to a quaternary ammonium salt at the same time, and (2) removing the tertiary amine and water produced from the system.

Examples of quaternary ammonium cations of the quaternary ammonium salts used in the invention can be tetraalkylammonium, tetraalkylphosphonium, imidazolium, pyrazolium, pyridinium, triazolium, pyridazinium, thiazolium, oxazolium, pyrimidinium, pyrazinium, etc.

The following compounds are specifically exemplified.

As tetraalkylammonium are tetraethylammonium, tetramethylammonium, tetrapropylammonium, tetrabutylammonium, triethylmethylammonium, trimethylethylammonium, dimethyldiethylammonium, trimethylpropylammonium, trimethylbutylammonium, dimethylethylpropylammonium, methylethylpropylbutylammonium, N,N-dimethylpyrrolidinium, N-ethyl-N-methylpyrrolidinium, N-methyl-N-propylpyrrolidinium, N-ethyl-N-propylpyrrolidinium, N,N-dimethylpiperidinium, N-methyl-N-ethylpiperidinium, N-methyl-N-propylpiperidinium, N-ethyl-N-propylpiperidinium, N,N-dimethylmorpholinium, N-methyl-N-ethylmorpholinium, N-methyl-N-propylmorpholinium, N-ethyl-N-propylmorpholinium, trimethylmethoxyammonium, dimethylethylmethoxymethylammonium, dimethylpropylmethoxymethylammonium, dimethylbutylmethoxymethylammonium, diethylmethymethoxymethylammonium, methylethylpropylmethoxymethylammonium, triethylmethoxymethylammonium, diethylpropylmethoxymethylammonium, diethylbutylmethoxymethylammonium, dipropylmethylmethoxymethylammonium, dipropylethylmethoxymethylammonium, tripropylmethoxymethylammonium, tributylmethoxymethylammonium, trimethylethoxymethylammonium, dimethylethylethoxymethylammonium, dimethylpropylethoxymethylammonium, dimethylbutylethoxymethylammonium, diethylmethylethoxymethylammonium, triethylethoxymethylammonium, diethylpropylethoxymethylammonium, diethylbutylethoxymethylammonium, dipropylmethylethoxymethylammonium, dipropylethylethoxymethylammonium, tripropylethoxymethylammonium, tributylethoxymethylammonium, N-methyl-N-methoxymethylpyrrolidinium, N-ethyl-N-methoxymethylpyrrolidinium, N-propyl-N-methoxymethylpyrrolidinium, N-butyl-N-methoxymethylpyrrolidinium, N-methyl-N-ethoxymethylpyrrolidinium, N-methyl-N-propoxymethylpyrrolidinium, N-methyl-N-butoxymethylpyrrolidinium, N-methyl-N-methoxymethylpiperidinium, N-ethyl-N-methoxymethylpyrrolidinium, N-methyl-N-ethoxymethylpyrrolidinium, N-propyl-N-methoxymethylpyrrolidinium, N-methyl-N-propoxymethylpyrrolidinium, 4-azoniaspiro[3,4]octane, 3-azoniaspiro[2,4]heptane, 5-azoniaspiro[5,5]undecane, etc.

As tetraalkylphosphonium are tetraethylphosphonium, tetramethylphosphonium, tetrapropylphosphonium, tetrabutylphosphonium, triethylmethylphosphonium, trimethylethylphosphonium, dimethyldiethylphosphonium, trimethylpropylphosphonium, trimethylbutylphosphonium, dimethylethylpropylphosphonium, methylethylpropylbutylphosphonium, etc.

As imidazolium are 1,3-dimethylimidazolium, 1-ethyl-3-methylimidazolium, 1,3-diethylimidazolium, 1,2-dimethyl-3-ethylimidazolium, 1,2-dimethyl-3-propylimidazolium, etc.

As pyrazolium are 1,2-dimethylpyrazolium, 1-methyl-2-ethylpyrazolium, 1-propyl-2-methypyrazolium, 1-methyl-2-butylpyrazolium, etc.

As pyridinium are N-methylpyridinium, N-ethylpyridinium, N-propylpyridinium, N-butylpyridinium, etc.

As triazolium are 1-methyltriazolium, 1-ethyltriazolium, 1-propyltriazolium, 1-butyltriazolium, etc.

As pyridazinium are 1-methylpyridazinium, 1-ethylpyridazinium, 1-propylpyridazinium, 1-butylpyridazinium, etc.

As thiazolium are 1,2-dimethylthiazolium, 1,2-dimethyl-3-propylthiazolium, etc.

As oxazolium are 1-ethyl-2-methyloxazolium, 1,3-dimethyloxazolium, etc.

As pyrimidinium are 1,2-dimethylpyrimidinium, 1-methyl-3-propylpyrimidinium, etc.

As pyrazinium are 1-ethyl-2-methylpyrazinium, 1-butylpyrazinium, etc.

Examples of anions of quaternary ammonium salts usable in the present invention are $CF_3CO_2^-$, $CF_3SO_3^-$, $BF_4^-$, $AlF_4^-$, $ClBF_3^-$, $(FSO_2)_2N^-$, $PF_6^-$, $AsF_6^-$, $ClO_4^-$, $N(CF_3SO_3)_2^-$, $C(CF_3SO_3)_3^-$, $RfSO_3^-$, $RfCO_2^-$, (Rf is fluoroalkyl having 1 to 8 carbon atoms), $(R^{r1}SO_2)(R^{r2}SO_2)N^-$ and $(R^{r1}SO_2)(R^{r2}CO_2)^-$ ($R^{r1}$ and $R^{r2}$ are the same or different and are each fluoroalkyl having 1 to 8 carbon atoms). Preferable are $CF_3CO_2^-$, $CF_3SO_3^-$, $BF_4^-$, $AlF_4^-$, $ClBF_3^-$ or $(FSO_2)_2N^-$.

Examples of quaternary ammonium cations of quaternary ammonium hydroxide salts or quaternary ammonium carbonates which are useful for the present invention are the same as those mentioned as quaternary ammonium cations of the foregoing quaternary ammonium salts.

Tertiary amine protonic acid salts which are impurities according to the present invention are produced when quaternary ammonium salts are produced. The acid salt is produced also when the quaternary ammonium salt is thermally decomposed. For example, in preparing $BF_4$ salt of N-methoxymethyl-N-methylpyrrolidinium, hydrochloric acid present as an impurity in chloromethyl methyl ether serving as a material reacts with methylpyrrolidine, a tertiary amine serving as another material, to produce protonic acid salt of methylpyrrolidine. Alternatively, chloromethyl methyl ether is hydrolyzed with a very small amount of water present in methylpyrrolidine or in a solvent to produce hydrochloric acid, permitting this acid to form protonic acid salt of methylpyrrolidine through the same reaction as above. Through a salt conversion reaction wherein $HBF_4$ is used, this protonic acid salt is made into $HBF_4$ salt of methylopyrrolidine which is very difficult to remove. Further when the $BF_4$ salt is prepared at a high temperature of 130 to 200° C., the thermal decomposition of N-methoxymethyl-N-methylpyrrolidinium salts (hudrochloride, $BF_4$ salt) produces methylpyrrolidine $HBF_4$ salt although in a small amount. Further when an excess of methylpyrrolidine is used, methylpyrrolidine remains in N-methoxymethyl-N-methylpyrrolidinium hydrochloride, and the subsequent conversion to $HBF_4$ salt produces N-methylpyrrolidinium $HBF_4$ salt.

As the tertiary amines, the following compounds are specifically exemplified.

Triethylamine, trimethylamine, tripropylamine, tributylamine, dimethylethylamine, dimethylpropylamine, dimethylbutylamine, diethylmethylamine, diethylpropylamine, diethylbutylamine, dipropylbutylamine, dibutylpropylamine, methylethylpropylamine, methylethylbutylamine, ethylprpylbutylamine, N-methylpyrrolidine, N-ethylpyrrolidine, N-propylpyrrolidine, N-butylpyrrolidine, N-methylpiperidine, N-ethylpiperidine, N-propylpiperidine, N-butylpiperidine, N-methylmorpholine, N-ethylmorpholine, N-propylmorpholine, N-butylmorpholine, dimethylmethoxymethylamine, diethylmethoxymethylamine, dipropylmethoxymethylamine, dibutylmethoxymethylamine, ethylmethylmethoxymethylamine, methylpropylmethoxymethylamine, methylbutylmethoxymethylamine, ethylpropylmethoxymethylamine, ethylbutylmethoxymethylamine, propylbutylmethoxymethylamine, dimethylethoxymethylamine, diethylethoxymethylamine, dipropylethoxymethylamine, dibutylethoxymethylamine, ethylmethylethoxymethylamine, methylpropylethoxymethylamine, ethylpropylethoxymethylamine, ethylbutylethoxymethylamine, propylbutylethoxymethylamine, N-methoxymethylpyrrolidine, N-ethoxymethylpyrrolidine, N-propoxymethylpyrrolidine, N-butoxymethylpyrrolidine, N-ethoxymethylpyrrolidine, N-propoxymethylpyrrolidine, etc.

Examples of imidazoles are 1-methylimidazole, 1-ethylimidazole, 1,2-dimethylimidazole, 1-methyl-2-ethylimidazole, etc.

Examples of pyrazoliums are 1-methylpyrazole, 1-ethylpyrazole, 1-propylpyrazole, 3-methylpyrazole, etc. Also exemplified are pyridine, triazole, pyridazine, pyrazine, 1-methylthiazole, 1-methyloxazole, etc.

Further, examples of protonic acid salts of the tertiary amines are protonic acid salts of the above tertiary amines, the protonic acids being $CF_3CO_2H$, $CF_3SO_3H$, $HBF_4$, $HAlF_4$, HClBF$_3$, (FSO$_2$)$_2$NH, HPF$_6$, HAsF$_6$, HClO$_4$, NH(CF$_3$SO$_3$)$_2$, HC(CF$_3$SO$_3$)$_3$, RfSO$_3$H, RfCO$_2$H (Rf is fluoroalkyl having 1 to 8 carbon atoms), (R$^{r1}$SO$_2$)(R$^{r2}$SO$_2$)NH and (R$^{r1}$SO$_2$)(R$^{r2}$CO$_2$)H (R$^{r1}$ and R$^{r2}$ are the same or different and are each fluoroalkyl having 1 to 8 carbon atoms).

A description will be given of the process of the invention for preparing a high-quality quaternary ammonium salt.

A tertiary amine serving as the starting material is reacted with an alkyl halide which may have a substituent to thereby produce a quaternary ammonium halide salt. The quaternary ammonium halide salt is then reacted with an acid compound to prepare a quaternary ammonium salt.

Examples of acid compounds are CF$_3$CO$_2$H, CF$_3$SO$_3$H, HBF$_4$, HAlF$_4$, HClBF$_3$, (FSO$_2$)$_2$NH, HPF$_6$, HAsF$_6$, HClO$_4$, NH(CF$_3$SO$_3$)$_2$, CH(CF$_3$SO$_3$)$_3$, RfSO$_3$H, RfCO$_2$H (Rf is fluoroalkyl having 1 to 8 carbon atoms), (R$^{r1}$SO$_2$) (R$^{r2}$SO$_2$)NH and (R$^{r1}$SO$_2$) (R$^{r2}$CO$_2$)H (R$^{r1}$ and R$^{r2}$ are the same or different and are each fluoroalkyl having 1 to 8 carbon atoms). Preferable are CF$_3$CO$_2$H, CF$_3$SO$_3$H, HBF$_4$, HAlF$_4$, HClBF$_3$ or (FSO$_2$)$_2$NH.

The quaternary ammonium salt obtained contains as an impurity a very small amount of a tertiary amine protonic acid salt derived from the starting material of tertiary amine.

Subsequently, a quaternary ammonium hydroxide salt or quaternary ammonium carbonate is added for reaction (neutralization) to the quaternary ammonium salt containing the impurity. The quaternary ammonium hydroxide salt or quaternary ammonium carbonate is added in an amount of 0.5 to 10 equivalents, preferably 0.5 to 2 equivalents, more preferably 1 to 2 equivalents based on the mole number of the tertiary amine protonic acid salt.

The addition is made at a temperature of −20° C. to 200° C., preferably 10° C. to 100° C., more preferably 25° C. to 80° C. The reaction time is 10 minutes to 20 hours, preferably 30 minutes to 5 hours.

The reaction converts the quaternary ammonium hydroxide salt or quaternary ammonium carbonate to a quaternary ammonium salt, and the tertiary amine protonic acid salt to a tertiary amine and water. The tertiary amine and water can be distilled off by a usual method, for example, by distillation in a vacuum or by heating, or by the combination of these methods. They are removable also by heating while introducing nitrogen, argon or air that will not react with the quaternary ammonium salt.

The tertiary amine and water are distilled off at a temperature of 20° C. to 200° C., preferably 90° C. to 170° C. for 0.5 to 24 hours, preferably 5 to 18 hours.

The quaternary ammonium salt resulting from the removal of impurities is reduced in the amounts of impurities, i.e., tertiary amine and tertiary amine protonic acid salt.

The high-purity quaternary ammonium salt prepared according to the present invention is favorably usable as an electrolyte or electrolytic solution, for example, in electric double layer capacitors, electrolytic capacitors and cells.

The smaller the content of the tertiary amine protonic acid salt in the electrolyte required of electrolytes for nonaqueous electrolysis, the better from the viewpoint of a reduction in the voltage resistance of electric double layer capacitors, electrolytic capacitors or cells and the diminution of the reliability thereof. The impurity content is preferably up to 200 ppm, more preferably up to 100 ppm, especially preferably 30 ppm, most preferably up to 10 ppm.

The concentration of the tertiary amine protonic acid salt can be determined by liquid chromatography. The liquid chromatographic analysis can be conducted, for example, under the following conditions.

Column Inertsil ODS-3 250 mm×4.6 mm I.D., 5.0 μm (product of GL Science), detector L-7490 R1 detector (product of Hitachi Ltd.), mobile phase [Na$_2$HPO$_4$ 1 mM+KH$_2$PO$_4$ 9 mM+NaClO$_4$ 100 mM]/H$_2$O, flow rate 1.0 ml/min., column temp. 40° C.

BEST MODE OF CARRYING OUT THE INVENTION

The present invention will be described with reference to the following Examples, but is not limited to these examples.

Example 1

To 100 g of N-methoxymethyl-N-methylpyrrolidinium tetrafluoroborate containing 410 ppm of N-methyl pyrrolidine.HBF$_4$ salt was added 0.2 g of an aqueous solution of N,N,N-triethyl-N-methylammonium hydroxide (35 wt. %) within a glove box having an argon atmosphere with a dew point of −60° C., and the mixture was reacted at 130° C. for 2 hours while introducing nitrogen thereinto at a rate of 5 L/min. The reaction mixture was thereafter held in a vacuum of 1 mmHg at 25° C. for 1 hour. The mixture was returned to atmospheric pressure with argon gas having a dew point of −60° C. and analyzed. The content of N-methyl pyrrolidine.HBF$_4$ salt was up to a detection limit (10 ppm).

Example 2

To 100 g of N-methoxymethyl-N-methylpyrrolidinium tetrafluoroborate containing 410 ppm of N-methyl pyrrolidine.HBF$_4$ salt was added 0.2 g of an aqueous solution of N,N,N-triethyl-N-methylammonium hydroxide (35 wt. %), and the mixture was reacted at 120° C. for 2 hours while introducing nitrogen thereinto at a rate of 5 L/min. The content of N-methylpyrrolidine.HBF$_4$ salt was up to a detection limit (10 ppm).

Example 3

To 100 g of N-methoxymethyl-N-methylpyrrolidinium tetrafluoroborate containing 410 ppm of N-methyl pyrrolidine.HBF$_4$ salt was added 0.23 g of N-methoxymethyl-N-methylpyrrolidinium hydroxide within a glove box having an argon atmosphere with a dew point of −60° C., and the mixture was reacted at 130° C. for 2 hours while introducing nitrogen thereinto at a rate of 5 L/min. The reaction mixture was thereafter held in a vacuum of 1 mmHg at 25° C. for 1 hour. The mixture was returned to atmospheric pressure with argon gas having a dew point of −60° C. and analyzed. The content of N-methylpyrrolidine.HBF$_4$ salt was up to a detection limit (10 ppm).

Example 4

To 100 g of N-methoxymethyl-N-methylpyrrolidinium tetrafluoroborate containing 410 ppm of N-methyl pyrrolidine.HBF$_4$ salt was added 1.0 g of an aqueous solution of N-methoxymethyl-N-methylpyrrolidinium hydroxide (5 wt. %), and the mixture was reacted at 120° C. for 2 hours while introducing nitrogen thereinto at a rate of 5 L/min. The reaction mixture was thereafter held in a vacuum of 1 mmHg at 25° C. for 1 hour. The content of N-methyl pyrrolidine.HBF$_4$ salt was up to a detection limit (10 ppm).

Example 5

A 50 mg quantity of triethylmethylammonium tetrafluoroborate containing 100 ppm of triethylamine.HBF$_4$ salt was dissolved in 70 g of methyl alcohol, 0.2 g of a methyl alcohol solution of N,N,N-triethyl-N-methylammonium hydroxide (20 wt. %) was added to the solution, and the mixture was reacted at 120° C. for 12 hours while introducing nitrogen thereinto at a rate of 5 L/min. The content of triethylamine.HBF$_4$ salt was up to a detection limit (10 ppm).

Example 6

A 50 mg quantity of triethylmethylammonium tetrafluoroborate containing 100 ppm of triethylamine.HBF$_4$ salt was dissolved in 50 g of water, 0.1 g of an aqueous solution of N,N,N-triethyl-N-methylammonium hydroxide (35 wt. %) was added to the solution, and the mixture was reacted at 120° C. for 12 hours while introducing nitrogen thereinto at a rate of 5 L/min. The content of triethylamine.HBF$_4$ salt was up to a detection limit (10 ppm).

INDUSTRIAL APPLICABILITY

According to the invention, the amounts of a tertiary amine and tertiary amine protonic acid salt contained as impurities in quaternary ammonium salts can be reduced.

The quaternary ammonium salt reduced in impurity contents is favorably usable as an electrolyte in electric double layer capacitors, electrolytic capacitors and like capacitor elements.

The electric double layer capacitor and electrolytic capacitor incorporating this electrolyte are improved in voltage resistance and long-term reliability.

The invention claimed is:

1. A process for preparing a highly pure quaternary ammonium salt comprising:
   (1) adding a quaternary ammonium hydroxide salt or quaternary ammonium carbonate to a quaternary ammonium salt containing a protonic acid salt of a tertiary amine as an impurity,
       wherein the anion of quaternary ammonium salt is selected from the group consisting of $CF_3CO_2^-$, $CF_3SO_3^-$, $BF_4^-$, $AlF_4^-$, $ClBF_3^-$, $(FSO_2)_2N^-$, $PF_6^-$, $AsF_6^-$, $ClO_4^-$, $N(CF_3SO_3)_2^-$, $C(CF_3SO_3)_3^-$, $RfSO_3^-$, $RfCO_2^-$, wherein Rf is fluoroalkyl having 1 to 8 carbon atoms; $(R^{r1}SO_2)(R^{r2}SO_2)N^-$ and $(R^{r1}SO_2)(R^{r2}CO_2)^-$, wherein $R^{r1}$ and $R^{r2}$ are the same or different and are each fluoroalkyl having 1 to 8 carbon atoms: and
       wherein the protonic acid is selected from the group consisting of $CF_3CO_2H$, $CF_3SO_3H$, $HBF_4$, $HAlF_4$, $HClBF_3$, $(FSO_2)_2NH$, $HPF_6$, $HAsF_6$, $HClO_4$, $NH(CF_3SO_2)_2$, $HC(CF_3SO_3)_3$, $RfSO_3H$, $RfCO_2H$, wherein Rf is fluoroalkyl having 1 to 8 carbon atoms; $(R^{r1}SO_2)(R^{r2}SO_2)NH$ and $(R^{r1}SO_2)(R^{r2}CO_2)H$, wherein $R^{r1}$ and $R^{r2}$ are the same or different and are each fluoroalkyl having 1 to 8 carbon atoms,
   and thereby neutralizing the tertiary amine protonic acid salt with the quaternary ammonium hydroxide salt or carbonate to convert the acid salt to a tertiary amine and water and to convert the quaternary ammonium hydroxide salt or carbonate to a quaternary ammonium salt at the same time, and
   (2) removing the tertiary amine and water produced from the system.

2. A process for preparing a highly pure quaternary ammonium salt comprising:
   (1) reacting a tertiary amine with an alkyl halide having or not having a substituent to obtain a quaternary ammonium halide salt,
   (2) reacting an acid compound with the halide salt to obtain a quaternary ammonium salt containing a tertiary amine protonic acid salt as an impurity,
       wherein the anion of quaternary ammonium salt is selected from the group consisting of $CF_3CO_2^-$, $CF_3SO_3^-$, $BF_4^-$, $AlF_4^-$, $ClBF_3^-$, $(FSO_2)_2N^-$, $PF_6^-$, $AsF_6^-$, $ClO_4^-$, $N(CF_3SO_3)_2^-$, $C(CF_3SO_3)_3^-$, $RfSO_3^-$, $RfCO_2^-$, wherein Rf is fluoroalkyl having 1 to 8 carbon atoms; $(R^{r1}SO_2)(R^{r2}SO_2)N^-$ and $(R^{r1}SO_2)(R^{r2}CO_2)^-$, wherein $R^{r1}$ and $R^{r2}$ are the same or different and are each fluoroalkyl having 1 to 8 carbon atoms: and
       wherein the protonic acid is selected from the group consisting of $CF_3CO_2H$, $CF_3SO_3H$, $HBF_4$, $HAlF_4$, $HClBF_3$, $(FSO_2)_2NH$, $HPF_6$, $HAsF_6$, $HClO_4$, $NH(CF_3SO_3)_2$, $HC(CF_3SO_3)_3$, $RfSO_3H$, $RfCO_2H$, wherein Rf is fluoroalkyl having 1 to 8 carbon atoms; $(R^{r1}SO_2)(R^{r2}SO_2)NH$ and $(R^{r1}SO_2)(R^{r2}CO_2)H$, wherein $R^{r1}$ and $R^{r2}$ are the same or different and are each fluoroalkyl having 1 to 8 carbon atoms,
   (3) adding a quaternary ammonium hydroxide salt or quaternary ammonium carbonate to the quaternary ammonium salt and thereby neutralizing the tertiary amine protonic acid salt with the quaternary ammonium hydroxide salt or carbonate to convert the acid salt to a tertiary amine and water and to convert the quaternary ammonium hydroxide salt or carbonate to a quaternary ammonium salt at the same time, and
   (4) removing the tertiary amine and water produced from the system.

3. A process as defined in claim 2 wherein the acid compound is $CF_3CO_2H$, $CF_3SO_3H$, $HBF_4$, $HAlF_4$, $HClBF_3$ or $(FSO_2)_2NH$.

* * * * *